(12) United States Patent
Ross et al.

(10) Patent No.: US 9,096,484 B1
(45) Date of Patent: Aug. 4, 2015

(54) BIMETALLIC CATALYST AND USE IN XYLENE PRODUCTION

(71) Applicant: ExxonMobil Chemical Patents Inc., Baytown, TX (US)

(72) Inventors: April D. Ross, Clinton, NJ (US); Jane C. Cheng, Bethlehem, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/669,179

(22) Filed: Mar. 26, 2015

Related U.S. Application Data

(62) Division of application No. 13/747,905, filed on Jan. 23, 2013, now Pat. No. 9,018,121.

(60) Provisional application No. 61/604,926, filed on Feb. 29, 2012.

(51) Int. Cl.
 | | |
 |---|---|
 | *C07C 5/22* | (2006.01) |
 | *C07C 5/27* | (2006.01) |
 | *C07C 5/25* | (2006.01) |
 | *C07C 15/08* | (2006.01) |

(52) U.S. Cl.
CPC .............. *C07C 5/2708* (2013.01); *C07C 5/222* (2013.01); *C07C 5/2556* (2013.01); *C07C 5/2737* (2013.01); *C07C 5/2754* (2013.01); *C07C 15/08* (2013.01); *C07C 2529/44* (2013.01)

(58) Field of Classification Search
USPC .................. 585/470, 471, 475, 481, 482, 489
See application file for complete search history.

(56) References Cited

U.S. PATENT DOCUMENTS

| | | |
|---|---|---|
| 4,485,185 A | 11/1984 | Onodera et al. |
| 4,899,011 A | 2/1990 | Chu et al. |
| 5,283,385 A | 2/1994 | Dessau |
| 5,689,027 A | 11/1997 | Abichandani et al. |
| 5,705,726 A | 1/1998 | Abichandani et al. |
| 6,028,238 A | 2/2000 | Beck et al. |
| 7,199,070 B2 | 4/2007 | Iwayama et al. |
| 7,247,762 B2 | 7/2007 | Stern |
| 7,270,792 B2 | 9/2007 | Deckman et al. |
| 7,271,118 B2 | 9/2007 | Raich et al. |
| 7,525,008 B2 | 4/2009 | Bogdan et al. |
| 7,626,065 B2 | 12/2009 | Ou et al. |
| 2001/0051754 A1 | 12/2001 | Lissy et al. |
| 2006/0030478 A1 | 2/2006 | Raich et al. |
| 2007/0060469 A1 | 3/2007 | Bogdan et al. |
| 2007/0060470 A1 | 3/2007 | Bogdan et al. |
| 2010/0048381 A1 | 2/2010 | Oh et al. |
| 2011/0190556 A1 | 8/2011 | Levin et al. |

FOREIGN PATENT DOCUMENTS

| | | |
|---|---|---|
| EP | 1 495 805 | 1/2005 |
| EP | 2 022 564 | 2/2009 |
| WO | WO 2006/022991 | 3/2006 |
| WO | WO 2007/037866 | 4/2007 |
| WO | WO 2009/034093 | 3/2009 |

*Primary Examiner* — Elizabeth Wood

(57) ABSTRACT

The invention is directed to a bimetallic catalyst system adapted for the manufacture of xylenes, a process for making said catalyst system, and to the process of manufacture of xylenes using said catalyst system, providing, in embodiments, improved selectivity by at least one of higher ethylene saturation and low xylene loss, decreased susceptibility to poisoning from feedstream impurities, and ability to operate at less severe conditions.

9 Claims, 4 Drawing Sheets

BIMETALLIC CATALYST AND USE IN XYLENE PRODUCTION

PRIORITY CLAIM

This application is a divisional of and claims priority to U.S. patent application Ser. No. 13/747,905, filed Jan. 23, 2013, now U.S. Pat. No. 9,018,121 and Provisional Application No. 61/604,926, filed Feb. 29, 2012, the disclosures of which are incorporated by reference in their entirety.

FIELD OF THE INVENTION

The invention relates to bimetallic catalysts used in the production of xylenes, and more specifically in ethylbenzene dealkylation-xylene isomerization systems to make paraxylenes.

BACKGROUND OF THE INVENTION

A typical aromatic hydrocarbon stream found in petrochemical plants and refineries, such as may be produced by reforming and cracking naphtha, includes the C8 aromatic hydrocarbon isomers ethylbenzene and the xylene isomers paraxylene, metaxylene, and orthoxylene. Paraxylene is relatively high value as compared with the other isomers because it is used as the main raw material for polyester fibers. Orthoxylene, useful such as for preparing phthalate esters for plasticizers, is relatively more valuable than metaxylene. Unfortunately, an equilibrium mixture of xylenes contains roughly twice as much metaxylene as para- or orthoxylene.

To recover paraxylene preferentially, typically a C8 aromatic hydrocarbon stream is processed through a paraxylene recovery stage, such as an adsorption process (e.g., a Parex™ or Eluxyl™ absorptive separation unit) or crystallization process, to recover a paraxylene-enriched stream and a paraxylene-depleted stream. The paraxylene-depleted stream can then be catalytically isomerized to equilibrium for recycle in the paraxylene recovery loop. Ethylbenzene needs to be removed from the loop and one way to do so is as explained below.

Typically the catalyst used to promote isomerization of a paraxylene-depleted stream comprises a zeolite supported with a metal component of Group 7-10 of the Periodic Table, e.g., platinum or rhenium. In addition to promoting isomerization between xylene isomers, ethylbenzene can be converted to benzene through a dealkylation reaction and subsequent hydrogenation of the coproduct ethylene, in the presence of such catalysts. One of the undesired side reactions is metal-catalyzed ring saturation and another is the production of C9+ aromatic hydrocarbons. Research into increasing the efficiency of the paraxylene recovery loop is very active, and in particular there is constant demand for a better catalyst.

Recent prior art related to isomerization processes includes U.S. Pat. Nos. 6,028,238; 7,247,762; 7,270,792; 7,271,118; 7,626,065; U.S. Patent Publication 2011-0190556; and U.S. application Ser. No. 13/081,351.

Bimetallic catalysts per se are well-known and used in many different refining and petrochemical processes, such as in transalkylation in the manufacture of xylenes and other xylene manufacturing processes.

WO2009034093 (US2010/0217057) teaches a new configuration of ZSM-5 having higher average silica to alumina ratio at the edges of each crystallite than in the center providing reduced xylene losses in ethylbenzene dealkylation, especially when combined with silica as binder and one or more hydrogenation metals selected from platinum, tin, lead, silver, copper, and nickel.

WO2007037866 (US2007/0060470) teaches a catalyst of certain combinations of platinum, tin, acidic molecular sieve and aluminum phosphate binder for isomerization and dealkylation activities with low naphthenes make.

U.S. Pat. No. 7,525,008 teaches isomerization of a C8 aromatic stream with a MTW-type zeolite catalyst containing platinum and optionally tin. The MTW type zeolite has a silica to alumina mole ratio of between about 20:1 and 45:1.

US 2011/0190556 teaches a xylene production process involving transalkylation of a C9+ aromatic hydrocarbon feedstock with a C6 and/or C7 aromatic hydrocarbon feedstock. The feedstocks are contacted in the presence of hydrogen with a catalyst system comprising a first bimetallic catalyst and, downstream thereof, a second bimetallic catalyst. The first bimetallic catalyst comprises a molecular sieve having a Constraint Index in the range of 3 to 12, such as ZSM-5, and the metals are selected from Groups 6 to 12 of the Periodic Table. The second bimetallic catalyst comprises a molecular sieve having a Constraint Index less than 3, such as ZSM-12, and the metals are selected from Groups 6 to 12 of the Periodic Table.

US 2010/0048381 teaches a catalyst for xylene isomerization including a carrier having a zeolite with a specified molar ratio of silica to alumina impregnated with or mixed with a metal salt, the carrier supported with a Group VIII metal, or a Group VII metal additionally supported with tin, bismuth, or lead.

US 2007/0060470 teaches a catalyst comprising platinum and tin for the isomerization of xylenes and dealkylation of ethylbenzene. A metal-containing molecular sieve having a silica to alumina ratio of at least 20:1 is taught.

Additional references of interest include U.S. Pat. No. 7,271,118 (WO 2006/022991); U.S. Pat. No. 7,199,070 (EP 1495805); U.S. Pat. Nos. 5,689,027; 5,283,385; 4,485,185; and EP 2022564.

However, none of the systems described above are concerned with processing paraxylene-depleted feed streams through multiple bed systems where the functions of dealkylation and isomerization can be separately managed for improved performance. Furthermore, increased metal selectivity (desired ethylene saturation versus undesired ring saturation), decreased metal migration and decreased susceptibility to sulfur poisoning are still sought after.

The present inventors have surprisingly discovered a bimetallic system for a dealkylation and isomerization of a paraxylene-depleted C8 aromatic hydrocarbon feed stream having low levels of at least one Group 8-10 metal and at least one additional metal that provides, in embodiments, high ethylene saturation and low xylene loss at low temperatures when compared with current state of the art catalysts.

SUMMARY OF THE INVENTION

The invention is directed to a bimetallic catalyst system adapted for the manufacture of xylenes, a process for making said catalyst system, and to the process of manufacture of xylenes using said catalyst system, providing, in embodiments, improved selectivity by at least one of higher ethylene saturation, lower xylene loss, decreased ring loss, decreased susceptibility to poisoning from feedstream impurities, and ability to operate at less severe conditions.

In embodiments the catalyst system according to the invention comprises a first bed comprising at least one first metal selected from Groups 7-10, and at least one second metal selected from silver, copper, ruthenium, indium and tin, dispersed on ZSM-5, and a second bed comprising at least one first metal selected from Groups 7-10, and at least one second metal selected from silver, copper, ruthenium, indium and tin, dispersed on supported ZSM-5, and to a process comprising contacting a paraxylene-depleted feed steam with said catalyst system in the presence of hydrogen. The ZSM-5 in the first bed is silicon-selectivated and the ZSM-5 in the second bed is not silicon-selectivated.

In embodiments the metals are added to the first bed by the Incipient Wetness (IW) technique and to the second bed by mulling.

In embodiments the support is selected from alumina, silica, aluminosilicates, clay, and combinations thereof.

In embodiments the process comprises contacting the first bed of the catalyst system with a paraxylene-depleted feed comprising C8 aromatics including ethylbenzene and xylene isomers, to convert a portion of the ethylbenzene to benzene and ethane, to produce a ethylbenzene-depleted intermediate stream, and then contacting the intermediate stream with the second bed of the catalyst system isomerize xylenes and provide a final product comprising an increased amount of paraxylene and decreased amount of ethylbenzene when compared with said feed.

In embodiments the catalyst system comprises a first bed comprising a catalyst made by adding at least one first metal selected from Groups 7-10 and at least one second metal, different from said first metal and selected from silver, copper, ruthenium, indium and tin by the Incipient Wetness (IW) technique to a selectivated ZSM-5 catalyst, and a second bed comprising a catalyst made by combining a metal solution comprising at least one first metal selected from Groups 7-10 and at least one second metal, different from said first metal and selected from silver, copper, ruthenium, indium and tin, and water and a ZSM-5 molecular sieve and mulling with a support such as alumina, silica, and combinations thereof, to distribute the material. The resultant composition is extruded and then dried, calcined, and steamed. The ZSM-5 in the second bed is not silicon-selectivated.

It is an object of the invention to provide a simple and reproducible method of manufacture of a catalyst system adapted for the conversion of ethylbenzene and isomerization of xylenes that avoids the problems of the prior art with respect to xylene loss by ring saturation and robustness of the catalyst system with respect to sulfur poisoning and severity of operating conditions.

These and other objects, features, and advantages will become apparent as reference is made to the following detailed description, preferred embodiments, examples, and appended claims.

BRIEF DESCRIPTION OF THE DRAWINGS

In the accompanying drawings, like reference numerals are used to denote like parts throughout the several views.

DETAILED DESCRIPTION

Figure 1:
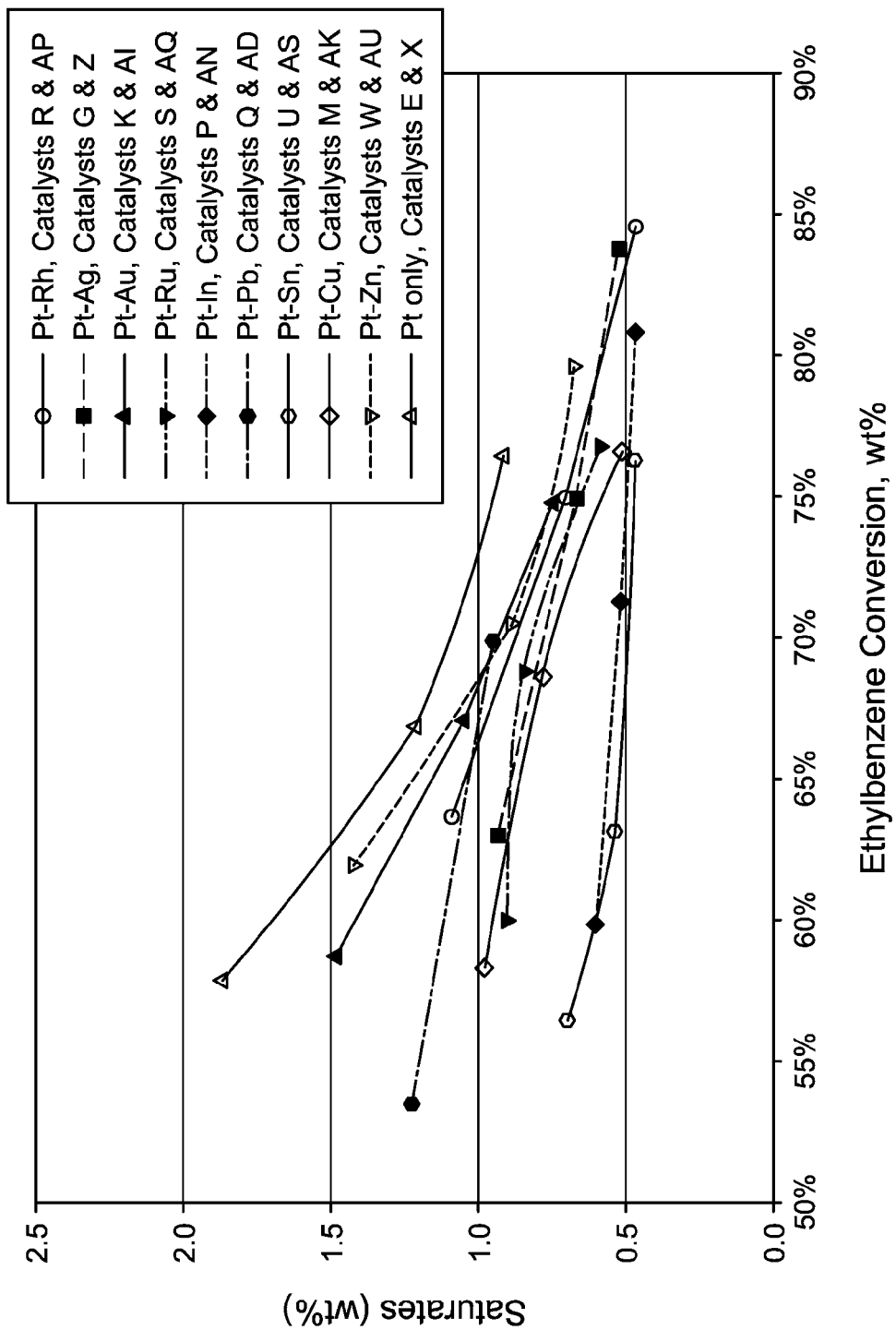
FIGS. 1-4 are plots comparing performance of bimetallic catalysts according to the present invention.

According to the invention, there is a bimetallic catalyst system adapted for the manufacture of xylenes from a paraxylene-depleted C8 aromatic hydrocarbon feedstream by dealkylation of ethylbenzene and isomerization of xylenes, a process for making said bimetallic catalyst system, and to the catalyst system used therein. In embodiments, the invention provides for improved selectivity by at least one of higher ethylene saturation and lower xylene loss, decreased susceptibility to poisoning from feedstream impurities, ability to operate at less severe conditions, and ease of preparation of the catalyst system.

The catalyst system is a two-bed system with a first bed comprising a catalyst adapted for dealkylation of ethylbenzene and a second bed comprising a catalyst adapted for isomerization. Each bed may be in series in separate reactors or in the same reactor. The separate catalysts are not mixed.

The invention may be better understood by reference to the following detailed examples, including experiments comparing catalysts according to the present invention with commercial catalysts of the prior art. The examples should be taken as representative of the present invention and not limiting thereof.

Terms and techniques used below should be well-known to the skilled artisan and unless defined specifically herein take definitions found in the prior art, particularly in those references discussed in the background or hereinbelow. Otherwise, The Handbook of Petroleum Refining Processes, $3^{rd}$ Edition; Robert Meyers, Editor; McGraw-Hill, ©2004, should be consulted before reference to other extraneous sources. However, for the avoidance of confusion the following description of certain terms is provided.

The Incipient Wetness (IW) technique is a well-known method of incorporating metals into materials; see, for instance, U.S. Pat. Nos. 4,302,359 and 7,271,118. Likewise, competitive ion exchange is a well-known method, such as discussed in the aforementioned U.S. Pat. No. 7,271,118.

Mulling refers to mixing of materials with sufficient liquid to form a paste and wherein the mixing is accompanied by shearing of the resultant mixture. Commercially available mullers may be used. See, for example, U.S. Pat. No. 7,335,802.

Selectivation—in situ silicon selectivation is discussed, for instance, in U.S. Pat. No. 5,475,179; ex situ silicon selectivation is discussed, for instance, in U.S. Pat. No. 5,625,103. Other selectivation agents to increase catalyst selectivity to paraxylene, such as carbon monoxide, are known; see for instance U.S. Pat. No. 7,902,414. The term "selectivated catalyst" as used herein means that the catalyst has been silicon selectivated, either by in situ silicon selectivation or by ex situ silicon selectivation, by means per se known in the art. In the present invention the first bed contains a catalyst that has been selectivated and the second bed contains a catalyst that has not been selectivated.

Hybrid calcination per se means calcination at a desired temperature and fixed total flow of air and nitrogen with gradual decrease of nitrogen and gradual increase of air. At the end of the hybrid calcination, the majority of the flow is air.

Alpha value is a well-known measure of acid activity and gives the relative rate constant for the rate of normal hexane conversion per volume of catalyst per unit time. See, for instance, U.S. Pat. No. 8,057,664.

By "para-depleted" is meant a mixture of C8 aromatic hydrocarbons having paraxylene present in an amount that is less than equilibrium value, the equilibrium value being approximately 23 to 24 wt % paraxylene based on total xylenes. A para-depleted mixture of xylenes results, for instance, from preferential removal of paraxylene by an adsorptive separation process such as by processing through a Parex™ or Eluxyl™ adsorptive separation unit, or by a crystallization process wherein the difference in freezing points of the C8 aromatic isomers is exploited. The term "para-depleted" is per se well known in the art.

Two-bed catalyst systems according to the present invention were prepared. All top bed (or first bed) catalysts were prepared using a silicon-selectivated H-ZSM-5 as a base and adding metals by Incipient Wetness (IW) technique. When two metals are used, the metal solution contained both metal sources. Tetraamine platinum nitrate was used as the platinum source for all catalysts. After being dried in ambient air, all catalysts were calcined for 3 hours at 660° F. in 40% Air in $N_2$ (~8.4% $O_2$). Top bed catalyst Alpha values (hexane cracking activity) are typically ~450. The bottom (or second bed) catalysts were not silicon-selectivated. To be sure, the designation "second bed" assumes that the stream to be treated contacts the "first bed" first and then contacts the second bed; likewise, the designation "bottom" bed and "top" bed assumes downward flow, top-to-bottom, although downward flow is not mandatory and other configurations can be envisioned by one of ordinary skill in the art.

TABLE 1

Top (First) Bed Catalyst Formulations

| Catalyst | Pt, wt % | 2nd Metal, (M) | 2nd Metal, wt % | Metal Precursor | Pt/M, Molar Ratio |
|---|---|---|---|---|---|
| E | 0.10 | None | — | — | — |
| F | 0.10 | Ag | 0.0276 | silver nitrate | 2/1 |
| G | 0.10 | Ag | 0.0553 | silver nitrate | 1/1 |
| H | 0.10 | Ag | 0.1106 | silver nitrate | 1/2 |
| I | 0.10 | Ag | 0.1659 | silver nitrate | 1/3 |
| J | 0.10 | Ag | 0.2212 | silver nitrate | 1/4 |
| K | 0.10 | Au | 0.1010 | Gold chloride | 1/1 |
| L | 0.10 | Cu | 0.0163 | copper nitrate hemipentahydrate | 2/1 |
| M | 0.10 | Cu | 0.0326 | copper nitrate hemipentahydrate | 1/1 |
| N | 0.10 | Cu | 0.0651 | copper nitrate hemipentahydrate | 1/2 |
| O | 0.10 | Cu | 0.0977 | copper nitrate hemipentahydrate | 1/3 |
| P | 0.10 | In | 0.0389 | Indium (III) Nitrate hydrate | 1/1 |
| Q | 0.10 | Pb | 0.1062 | Lead nitrate | 1/1 |
| R | 0.10 | Rh | 0.0527 | Rhodium Chloride | 1/1 |
| S | 0.10 | Ru | 0.0264 | Ru Chloride | 1/1 |
| T | 0.10 | Sn | 0.0304 | tin (II) chloride | 2/1 |
| U | 0.10 | Sn | 0.0608 | tin (II) chloride | 1/1 |
| V | 0.10 | Sn | 0.1217 | tin (II) chloride | 1/2 |
| W | 0.10 | Zn | 0.0335 | Zinc nitrate hexahydrate | 1/1 |

Bottom bed (or second bed) catalysts were made by extruding 80% H-ZSM-5 with 20% LaRoche Alumina Versal™ 300. Metal solution and water were all added during mulling. For all catalysts except AG, the order of addition into the muller was add crystal and mull to distribute, then add alumina and mull, then add metal solution and mull, and finally add water and mull. For Catalyst AG, the order of addition was add crystal and mull to distribute, then add metal solution and mull, then add alumina and mull, and finally add water and mull. Catalysts were extruded to 1/16" cylinders. After extrusion, extrudates were dried, then hybrid calcined at 1000° F. for 6 hours (80% Air, ~16.8% $O_2$), and finally steamed at 950° F. for 4 hours. Bottom bed catalyst alphas (hexane cracking activity) are typically ~95.

TABLE 2

Bottom Bed Catalyst Formulations

| Catalyst | Pt, wt % | 2nd Metal, (M) | 2nd Metal, wt % | Metal Precursor | Pt/M, Molar Ratio |
|---|---|---|---|---|---|
| X | 0.115 | None | — | — | — |
| Y | 0.115 | Ag | 0.0318 | silver nitrate | 2/1 |
| Z | 0.115 | Ag | 0.0636 | silver nitrate | 1/1 |
| AA | 0.115 | Ag | 0.1272 | silver nitrate | 1/2 |
| AB | 0.115 | Ag | 0.1908 | silver nitrate | 1/3 |
| AC | 0.115 | Ag | 0.2543 | silver nitrate | 1/4 |
| AD | 0.100 | Ag | 0.1106 | silver nitrate | 1/2 |
| AE | 0.100 | Ag | 0.1659 | silver nitrate | 1/3 |
| AF | 0.100 | Ag | 0.2212 | silver nitrate | 1/4 |
| AG* | 0.100 | Ag | 0.1659 | silver nitrate | 1/3 |
| AH | 0.075 | Ag | 0.1244 | silver nitrate | 1/3 |
| AI | 0.115 | Au | 0.1161 | Gold chloride | 1/1 |
| AJ | 0.115 | Cu | 0.0187 | copper nitrate hemipentahydrate | 2/1 |
| AK | 0.115 | Cu | 0.0375 | copper nitrate hemipentahydrate | 1/1 |
| AL | 0.115 | Cu | 0.7490 | copper nitrate hemipentahydrate | 1/2 |
| AM | 0.115 | Cu | 0.1124 | copper nitrate hemipentahydrate | 1/3 |
| AN | 0.115 | In | 0.0677 | Indium (III) Nitrate hydrate | 1/1 |
| AO | 0.115 | Pb | 0.1221 | Lead nitrate | 1/1 |
| AP | 0.115 | Rh | 0.0607 | Rhodium Chloride | 1/1 |
| AQ | 0.115 | Ru | 0.0596 | Ru Chloride | 1/1 |
| AR | 0.115 | Sn | 0.0350 | tin (II) chloride | 2/1 |
| AS | 0.115 | Sn | 0.0700 | tin (II) chloride | 1/1 |
| AT | 0.115 | Sn | 0.1400 | tin (II) chloride | 1/2 |
| AU | 0.115 | Zn | 0.0386 | Zinc nitrate hexahydrate | 1/1 |

Initial Dual-Bed Screening was then conducted, as described below.

Catalysts were tested in a fixed-bed micro unit. A total of 2 grams of catalyst (prepared as described above, "as-is") was loaded into reactors: 0.5 grams of top bed and 1.5 grams of bottom bed. The reactor pressure was 225 psig (1551 kPa) and the $H_2$:HC ratio was 1:1. The total feed flow rate, expressed as grams feed per gram catalyst per hour (WHSV) was 12 hr−1. The activity of the catalysts was determined as a function of reactor temperature (660 to 730° F. or 349 to 388° C.). The temperature range allowed comparison across a range of ethylbenzene conversions, from about 55 to 85 wt %. The feed to the reactor contained mostly C8 aromatic hydrocarbons with approximately 16% ethylbenzene. A detailed analysis of the feed is shown in Table 3. The catalysts were reduced in hydrogen for 1 hour at 400° C. prior to the introduction of feed. No sulfiding was performed. Product analysis occurred using on-line GC-FID with a 60-M DB-WAX column Saturates in the product (wt %) was used to indicate relative ring saturation activity of the different catalyst systems.

The catalysts with 1:1 molar ratio of Pt to the second metal were tested. All metal combinations showed some improvement over Pt only. Indium and tin showed the most reduction in saturates, followed by Cu, Ag, Rh, and Ru. Results for the various two-metal systems studied are shown in FIG. 1.

TABLE 3

Feed Properties

| FeedComponent | wt % |
|---|---|
| C5− | 0.1 |
| Saturates | 0.3 |

TABLE 3-continued

Feed Properties

| FeedComponent | wt % |
|---|---|
| Benzene | 0.0 |
| Toluene | 1.2 |
| Ethylbenzene | 16.3 |
| Para Xylene | 2.0 |
| Meta Xylene | 64.7 |
| Ortho Xylene | 15.4 |
| Total C9+ | 0.0 |

Secondary Dual-Bed Testing was then performed as described below.

A second series of fixed-bed micro unit testing was performed on select catalyst systems including Pt—Sn, Pt—Ag, and Pt—Cu catalysts made according to the present invention. A second GC column (DB-1) was added to the GC configuration to allow more detailed analysis, included quantification of the ethylene saturation activity through the ethane/ethylene ratio, and yield calculations. A total of 2 grams of the specified catalyst ("as-is") was loaded into reactors. The bimetallics used 0.5 grams of top bed and 1.5 grams of bottom bed. The reactor pressure was 225 psig (1551 kPa) and the $H_2$:HC ratio was 1:1. The total feed flow rate, expressed as grams feed per gram catalyst per hour (WHSV) was 12 hf$^{-1}$ for all catalysts. The activity of the catalysts was determined as a function of reactor temperature. The feed to the reactor contained mostly C8 aromatic hydrocarbons with approximately 16% ethylbenzene. A detailed analysis of the feed is shown in Table 4. The catalysts were not sulfided. All catalysts tested were de-edged for 24 hours at 430° C., $H_2$:HC ratio of 0.9:1, and pressure 185 psig (1275 kPa) before moving to the temperature scan from 640/650° F. to 745/755° F. Products were analyzed using an on-line GC-FID with a 60-M DB-WAX column and a DB-1 column (each of the designated columns, DB-WAX and DB-1, per se known in the art and commercially available). Typically the desired level of ethylbenzene conversion ("EBC") is >70%.

Figure 2:
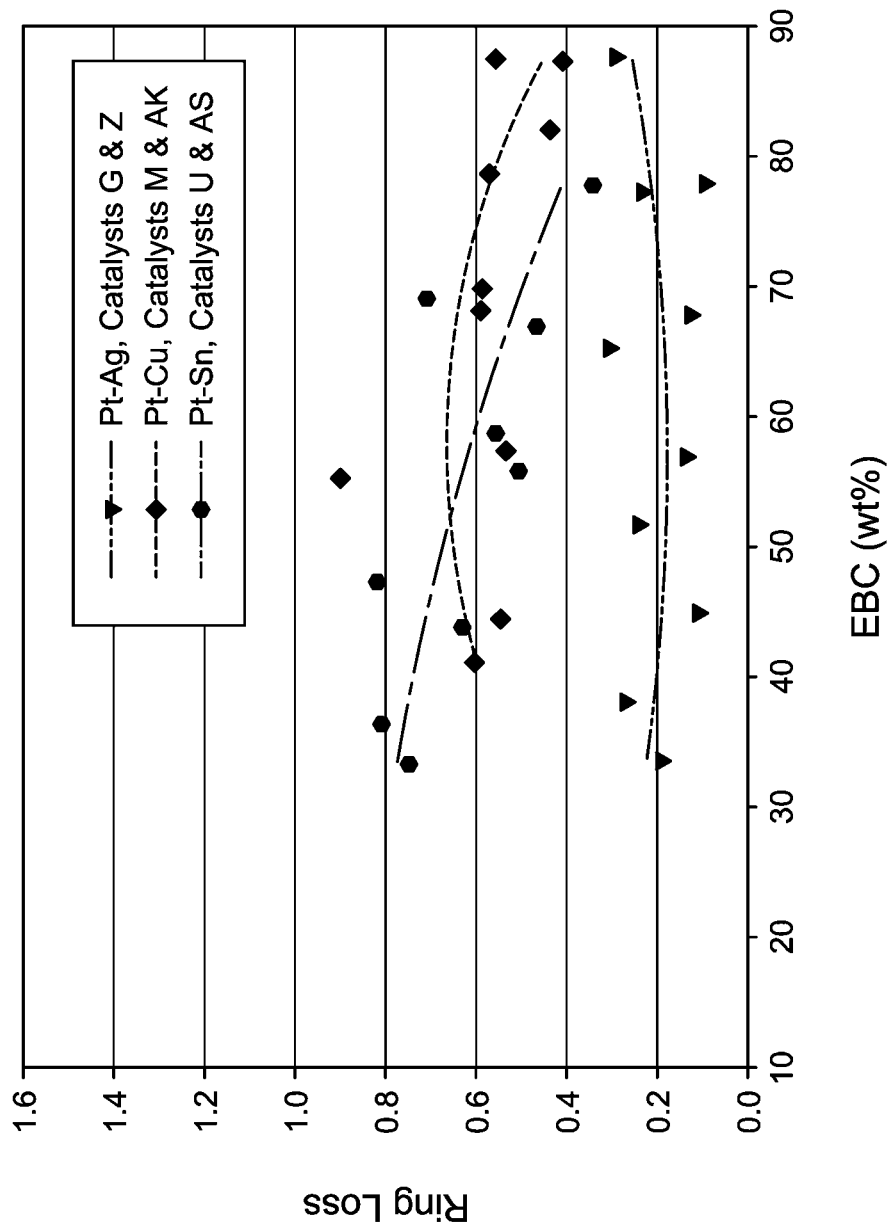
Figure 3:
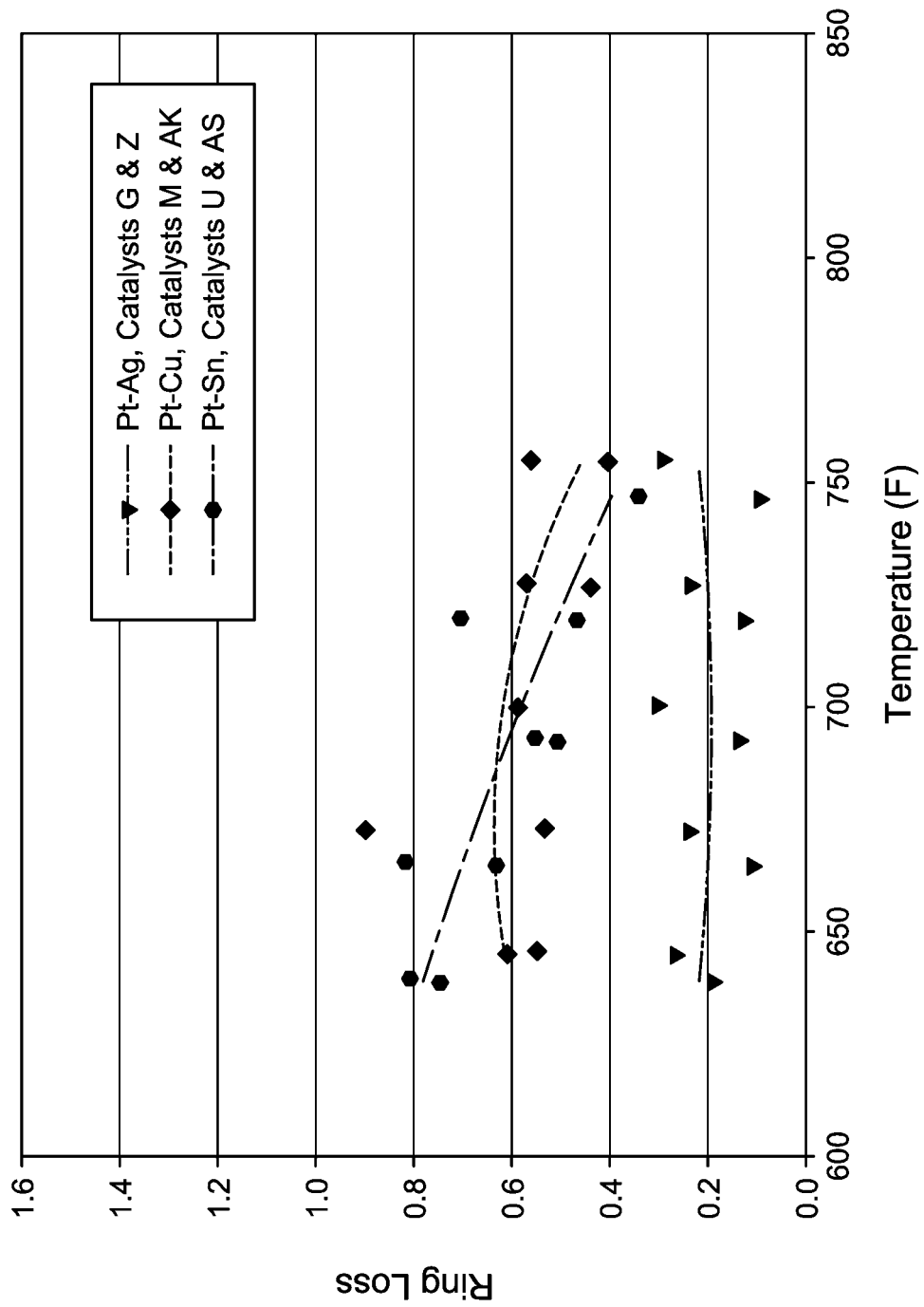
Figure 4:
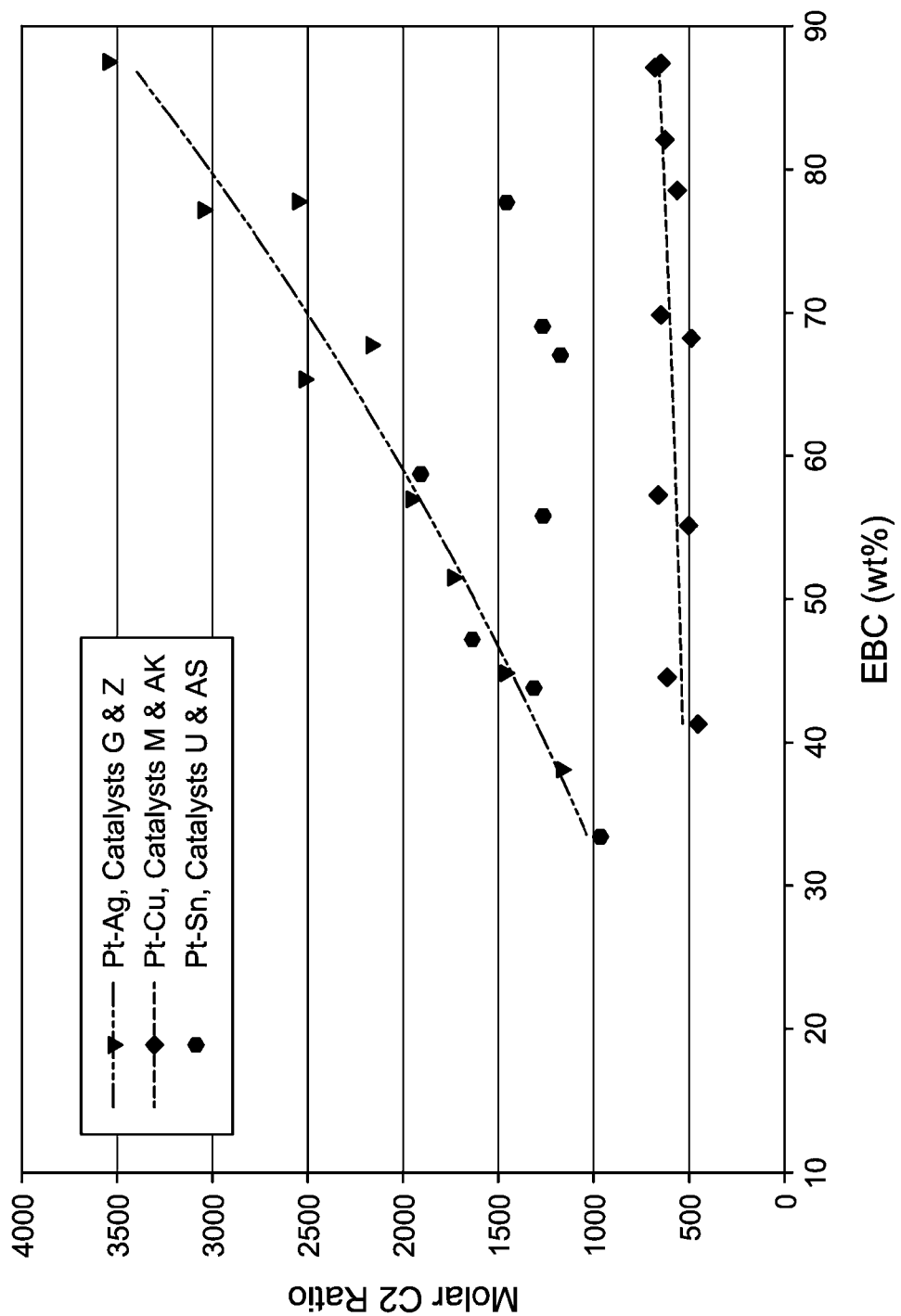

Comparison of certain two-metal systems of the present invention having 1:1 Pt:M catalysts for M=Ag, Cu, and Sn are shown in FIGS. 2-4; specifically with respect to ring loss versus ethylbenzene conversion (FIG. 2), ring loss versus temperature (FIG. 3) and molar C2 ratio (ethane/ethylene ratio; FIG. 4).

All the catalysts had low ring loss (low aromatics saturation) and high C2/C2=molar ratio (high ethylene saturation).

TABLE 4

Feed Properties

| | |
|---|---|
| Benzene | 0 |
| Toluene | 1.2 |
| Saturates | 0.14 |
| Ethyl benzene | 16.3 |
| Ortho Xylene | 15.3 |
| Meta Xylene | 65.1 |
| Para Xylene | 1.9 |
| Total C9+ | 0.01 |

CATALYST PREPARATION

Example 1

Top-Bed Catalyst Preparation: 0.1 wt % Pt and 1:0 Pt/Ag Molar Ratio

The catalyst used for top-bed catalyst preparation was H-ZSM-5 with 35% silica binder in a 1/16" (approximately 0.16 cm) cylindrical extrudate form. The H-ZSM-5 was selectivated three times with silicone before metal impregnation. An impregnation solution made with 1.41 g of tetraamine platinum nitrate solution (an aqueous solution with 3.55 wt % Pt) and 16.7 g of de-ionized (DI) water was slowly added to 50 g of the catalyst. The mixture was tumbled thoroughly until completely loose. The mixture was air-dried first at ambient conditions then at 250° F. for four hours. The mixture was calcined at 660° F. (352° C.) for 3 hours with a mixture of 40% air and 60% nitrogen at a flow rate of 5 vol/vol/min.

Example 2

Top-Bed Catalyst Preparation: 0.1 wt % Pt and 1:1 Pt/Ag Molar Ratio

The same procedure described in Example 1 was followed except that the impregnation solution was made with the composition below:
  1.41 g of tetraamine platinum nitrate solution (an aqueous solution with 3.55 wt % Pt)
  0.0446 g of chemical grade silver nitrate, solid
  16.7 g of DI water

Example 3

Top-Bed Catalyst Preparation: 0.1 wt % Pt and 1:2 Pt/Ag Molar Ratio

The same procedure described in Example 1 was followed except that the catalyst used was 100 g and the impregnation solution was made with the composition below:
  2.83 g of tetraamine platinum nitrate solution (an aqueous solution with 3.55 wt % Pt)
  0.175 g of chemical grade silver nitrate, solid
  26.2 g of DI water

Example 4

Top-Bed Catalyst Preparation: 0.1 wt % Pt and 1:3 Pt/Ag Molar Ratio

The same procedure described in Example 3 was followed except that the impregnation solution was made with the composition below:
  2.83 g of tetraamine platinum nitrate solution (an aqueous solution with 3.55 wt % Pt)
  0.265 g of chemical grade silver nitrate, solid
  26.2 g of DI water

Example 5

Top-Bed Catalyst Preparation: 0.1 wt % Pt and 1:4 Pt/Ag Molar Ratio

The same procedure described in Example 3 was followed except that the impregnation solution was made with the composition below:

2.83 g of tetraamine platinum nitrate solution (an aqueous solution with 3.55 wt % Pt)
0.36 g of chemical grade silver nitrate, solid
27.5 g of DI water

Example 6

Bottom-Bed Catalyst Preparation: 0.115 wt % Pt and 1:0 Pt/Ag Molar Ratio

Extrusion:

A mixture of 400 g of H-ZSM-5 crystal and 100 g Versal 300 was mulled thoroughly in a Muller. A 271 g of DI water was added to the mixture while mulling. An impregnation solution made with the following composition was added to the mixture while mulling.
16.22 g of tetraamine platinum nitrate solution (an aqueous solution with 3.55 wt % Pt)
120 g of DI water The metal-impregnated mixture was extruded with a 1/16" cylinder die plate. The extrudate was dried at 250° F.

Calcination:

The extrudate was heated in flowing nitrogen (5 vol/vol/min) at 150° F./h to 900° F. (482° C.), hold at 900° F. for 3 hr. While at 900° F., the gas mixture was changed to 0.25 vol/vol/min air+4.75 vol/vol/min nitrogen, hold for 30 min; 0.50 vol/vol/min air+4.50 vol/vol/min nitrogen, hold for 30 min; 1.0 vol/vol/min air+4.0 vol/vol/min nitrogen, hold for 30 min; 2.0 vol/vol/min air+3.0 vol/vol/min nitrogen, hold for 30 min. The temperature was increased at 150° F./h (83.3° C./h) to 1000° F. (538° C.). Once stabilized 1000° F., the gas mixture was changed to 4 vol/vol/min air+1 vol/vol/min nitrogen and hold for 6 hours. Cool down to ambient conditions and discharge.

Steaming:

The calcined catalyst was heated in flowing nitrogen (5 vol/vol/min) at 150° F./h to 900° F., hold at 900° F. for 30 min. Switch to steam over a 30 min period. Increase temperature at 150° F./h to 950° F. (510° C.), and then hold for 4 hours in 100% steam. Cool down in air and discharge.

Example 7

Bottom-Bed Catalyst Preparation: 0.115 wt % Pt and 1:1 pt/Ag Molar Ratio

The three-step procedure described in Example 6 was followed except that the impregnation solution was made with the composition below:
16.22 g of tetraamine platinum nitrate solution (an aqueous solution with 3.55 wt % Pt)
0.502 g of chemical grade silver nitrate, solid
120 g of DI water

Example 8

Bottom-Bed Catalyst Preparation: 0.115 wt % Pt and 1:2 Pt/Ag Molar Ratio

The three-step procedure described in Example 6 was followed except that the impregnation solution was made with the composition below:
16.22 g of tetraamine platinum nitrate solution (an aqueous solution with 3.55 wt % Pt)
1.004 g of chemical grade silver nitrate, solid
120 g of DI water

Example 9

Bottom-Bed Catalyst Preparation: 0.1 wt % Pt and 1:3 Pt/Ag Molar Ratio

The three-step procedure described in Example 6 was followed except that the impregnation solution was made with the composition below:
14.10 g of tetraamine platinum nitrate solution (an aqueous solution with 3.55 wt % Pt)
1.310 g of chemical grade silver nitrate, solid
120 g of DI water

Example 10

Bottom-Bed Catalyst Preparation: 0.1 wt % Pt and 1:4 Pt/Ag Molar Ratio

The three-step procedure described in Example 6 was followed except that the impregnation solution was made with the composition below:
14.10 g of tetraamine platinum nitrate solution (an aqueous solution with 3.55 wt % Pt)
1.746 g of chemical grade silver nitrate, solid
120 g of DI water Catalyst evaluation in fixed-bed micro units is described below.

Example 11

Evaluation of Pt/ZSM-5 Catalysts with 1:0 Pt/Ag

A fixed bed reactor with 3/8" external diameter was used for the evaluation. The reactor was equipped with a 1/8" diameter thermal well to monitor reactor temperature at the center of the catalyst bed. The catalysts in the shape of cylindrical 1/16" extrudate were loaded to the reactor based on the catalyst information provided in the table below.

| Catalyst | Pt, wt% | Pt/Ag (mole ratio) | Cat Wt |
|---|---|---|---|
| Top Bed, Example 1 | 0.100 | 1:0 | 0.5 g |
| Bottom Bed, Example 6 | 0.115 | 1:0 | 1.5 g |

The reactor pressure was set at 225 psig with a steady flow of $H_2$ at 92 cc/min. The reactor temperature was increased at 0.833° C./min to 200° C., and held at 200° C. for 16 hours. The temperature was further increase at 0.833° C./min to 380° C., and held at 380° C. for 3 hours. The feed was introduced at 27.6 cc/hr (12 WHSV). This feed rate was maintained through the entire run. The feed composition is show in the table below. The feed density was 0.87 g/cc.

| Feed Component | Weight, % |
|---|---|
| Toluene | 0.59 |
| Ethylbenzene | 14.75 |
| O-Xylene | 18.24 |
| M-Xylene | 62.72 |
| P-Xylene | 2.51 |
| Propylbenzene | 0.01 |
| Isopropylbenzene | 0.04 |
| 1-Methy-3-ethylbenzene | 0.01 |
| 1-Methy-4-ethylbenzene | 0.01 |
| 1,4-Diethylbenzene | 0.01 |
| Other C10 Aromatics | 0.01 |
| C11 Aromatics | 1.13 |
| Total | 100.00 |

The reactor pressure was then decreased to 185 psig, the $H_2$ flow was reduced to 82 cc/min, and reactor temperature was increase at 0.833° C./min to 430° C., and held at 430° C. for 24 hours.

The reactor pressure was increased to 225 psig, the $H_2$ flow was increased to 92 cc/min, and reactor temperature was reduced to 340° C., and held for 12 hours at 340° C. for data collection by online GC analysis. The reactor temperature was further increased at 0.833° C./min to 355, 370, 385, and 400° C. consecutively and held for 12 hours at each temperature setting for data collection by online GC analysis. The results are compared with the rest of the catalysts in the Discussions Section.

Example 12

Evaluation Pt/ZSM-5 Catalysts with 1:1 Pt/Ag

The same procedure described in Example 1 was followed to evaluate the second set of catalysts described in the table below. The results are compared with the rest of the catalysts in the Discussions section.

| Catalyst | Pt, wt % | Pt/Ag (mole ratio) | Cat Wt |
| --- | --- | --- | --- |
| Top Bed, Example 2 | 0.100 | 1:1 | 0.5 g |
| Bottom Bed, Example 7 | 0.115 | 1:1 | 1.5 g |

Example 13

Evaluation of Pt/ZSM-5 Catalysts with 1:2 Pt/Ag

The same procedure described in Example 1 was followed to evaluate the third set of catalysts described in the following table. The results are compared with the rest of the catalysts in the Discussions section.

| Catalyst | Pt, wt % | Pt/Ag (mole ratio) | Cat Wt |
| --- | --- | --- | --- |
| Top Bed, Example 3 | 0.100 | 1:2 | 0.5 g |
| Bottom Bed, Example 8 | 0.115 | 1:2 | 1.5 g |

Example 14

Evaluation of Pt/ZSM-5 Catalysts with 1:3 Pt/Ag

The same procedure described in Example 1 was followed to evaluate the fourth set of catalysts described in the following table. The results are compared with the rest of the catalysts in the Discussions section.

| Catalyst | Pt, wt % | Pt/Ag (mole ratio) | Cat Wt |
| --- | --- | --- | --- |
| Top Bed, Example 4 | 0.100 | 1:3 | 0.5 g |
| Bottom Bed, Example 9 | 0.100 | 1:3 | 1.5 g |

Example 15

Evaluation of Pt/ZSM-5 Catalysts with 1:4 Pt/Ag

The same procedure described in Example 1 was followed to evaluate the fifth set of catalysts described in the following table. The results are compared with the rest of the catalysts in the Discussions section.

| Catalyst | Pt, wt % | Pt/Ag (mole ratio) | Cat Wt |
| --- | --- | --- | --- |
| Top Bed, Example 5 | 0.100 | 1:4 | 0.5 g |
| Bottom Bed, Example 10 | 0.100 | 1:4 | 1.5 g |

Table 5 shows the micro unit results at EB conversion around 75%. When compared with the Ag-free catalyst, all Ag-containing catalysts had reduced production of $C_5{}^-$, $C_6{}^+$ non-aromatics, and $C_9{}^+$ aromatics as well as lower xylene loss and ring loss. All Ag-containing catalysts also had higher benzene selectivity from EB.

TABLE 5

Comparison of Catalyst Performance

| | | | | | |
| --- | --- | --- | --- | --- | --- |
| Pt loading, wt % Top bed/btm bed | | 0.100/ 0.115 | 0.100/ 0.115 | 0.100/ 0.115 | 0.100/ 0.100 | 0.100/ 0.100 |
| Pt/Ag Molar ratio (abbreviation) | | 1:0 (0x Ag) | 1:1 (1x Ag) | 1:2 (2x Ag) | 1:3 (3x Ag) | 1:4 (4x Ag) |
| Temperature, ° C. | | 386 | 384 | 384 | 397 | 396 |
| Temperature, ° F. | | 726 | 724 | 724 | 746 | 746 |
| Pressure, psig | | 233 | 233 | 234 | 225 | 218 |
| Feed flow rate, WHSV | | 12 | 12 | 12 | 12 | 12 |
| $H_2$/HC Molar ratio | | 1 | 1 | 1 | 1 | 1 |
| Time on stream, hr | | 70.5 | 74.5 | 70.5 | 82.5 | 82.5 |
| EB Conversion, % | | 74.1 | 77.6 | 75.5 | 78.9 | 73.8 |
| Product Distribution, wt % | (feed) | | | | | |
| $H_2$ | 0.00 | −0.39 | −0.25 | −0.23 | −0.22 | −0.20 |
| $C_5{}^-$ (light hydrocarbons) | 0.00 | 4.37 | 3.50 | 3.27 | 3.36 | 3.08 |
| $C_6{}^+$ Non-aromatics | 0.00 | 1.11 | 0.42 | 0.41 | 0.32 | 0.31 |
| $C_9{}^+$ Aromatics | 1.19 | 1.59 | 0.88 | 0.92 | 1.02 | 1.08 |
| Benzene | 0.00 | 6.45 | 7.90 | 7.45 | 8.08 | 7.47 |
| Toluene | 0.59 | 2.57 | 2.22 | 2.10 | 2.45 | 2.28 |
| p-Xylene | 2.51 | 19.22 | 19.30 | 19.40 | 19.70 | 19.67 |
| o-Xylene | 18.24 | 18.20 | 18.51 | 18.58 | 18.69 | 18.72 |

TABLE 5-continued

Comparison of Catalyst Performance

| | | | | | |
|---|---|---|---|---|---|
| Pt loading, wt % Top bed/btm bed | | 0.100/ 0.115 | 0.100/ 0.115 | 0.100/ 0.115 | 0.100/ 0.100 | 0.100/ 0.100 |
| Pt/Ag Molar ratio (abbreviation) | | 1:0 (0x Ag) | 1:1 (1x Ag) | 1:2 (2x Ag) | 1:3 (3x Ag) | 1:4 (4x Ag) |
| m-Xylene | 62.72 | 43.05 | 44.20 | 44.47 | 43.49 | 43.71 |
| EB | 14.75 | 3.83 | 3.31 | 3.62 | 3.10 | 3.87 |
| Total | 100.0 | 100.0 | 100.0 | 100.0 | 100.0 | 100.0 |
| p-Xylene + m-Xylene | 65.23 | 62.27 | 63.50 | 63.87 | 63.19 | 63.39 |
| Total xylenes | 83.49 | 80.47 | 82.02 | 82.45 | 81.89 | 82.11 |
| $C_2/C_2^=$, Molar ratio | | 2510 | 2746 | 2592 | 2666 | 1242 |
| Xylene loss [1], wt % | | 3.59 | 1.74 | 1.22 | 1.89 | 1.62 |
| Ring loss [2], mole % | | 2.41 | 0.40 | 0.35 | 0.11 | 0.09 |
| PXAE [3] | | 101.5 | 99.8 | 99.7 | 102.5 | 102.0 |
| Benzene Sel from EB [4],% | | 79.9 | 93.5 | 90.7 | 93.9 | 93.0 |

[1] Xylene loss = 100 × (feed xylene-product xylene)/feed xylene.
[2] Ring loss = 100 × (total aromatic carbon in feed-total aromatic carbon in products)/total aromatic carbon in feed.
[3] p-Xylene approaching equilibrium.
[4] Benzene Selectivity from EB = 100 × (Product benzene-Feed benzene)/(Feed EB-Product EB).

While the illustrative embodiments of the invention have been described with particularity, it will be understood that various other modifications will be apparent to and can be readily made by those skilled in the art without departing from the spirit and scope of the invention.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. A process comprising contacting a paraxylene-depleted C8 aromatic hydrocarbon feed including ethylbenzene and xylene isomers with a catalyst system to provide a final product comprising an increased amount of paraxylene and decreased amount of ethylbenzene when compared with said feed, wherein said catalyst system comprises a first bed including at least one first metal selected from platinum, rhenium, and mixtures thereof in an amount from about 0.1 to 0.3 wt. %, and at least one second metal selected from silver, copper, ruthenium, indium and tin, dispersed on ZSM-5, and a second bed including at least one first metal selected from platinum, rhenium, and mixtures thereof in an amount from about 0.1 to 0.3 wt. %, and at least one second metal selected from silver, copper, ruthenium, indium and tin, dispersed on ZSM-5, further characterized in that ZSM-5 in the first bed is silicon-selectivated and ZSM-5 in the second bed is not silicon-selectivated, and the ratio of the first metal to the second metal in the first bed and the second bed is from 1:1 to 1:4.

2. The process according to claim 1, wherein at least one of said first bed and said second bed further comprises a support selected independently from at least one of alumina, silica, aluminosilicates, clay, and combinations thereof.

3. The process according to claim 1, further characterized as including a first bed comprising a catalyst made by adding at least one first metal selected from platinum, rhenium, and mixtures thereof and at least one second metal selected from silver, copper, ruthenium, indium and tin by the incipient wetness technique to a silicone-selectivated ZSM-5, followed by drying and calcination, and a second bed comprising a catalyst made by combining a metal solution comprising at least one first metal selected from platinum, rhenium, and mixtures thereof and at least one second metal selected from silver, copper, ruthenium, indium and tin, and water and a non-selectivated ZSM-5 molecular sieve and mulling with a support, followed by extrusion, drying, calcination, and steaming.

4. The process according to claim 1, wherein said first bed comprises at least one second metal selected from silver, copper, tin, and mixtures thereof, and said second bed comprises at least one second metal selected from silver, copper, tin, and mixtures thereof.

5. The process according to claim 1, wherein said first bed comprises at least one second metal selected from silver, tin, and mixtures thereof, and said second bed comprises at least one second metal selected from silver, tin, and mixtures thereof.

6. The process according to claim 1, wherein said first metal in said first bed is rhenium and said first metal in said second bed is rhenium.

7. The process according to claim 1, wherein said second metal in said first bed is silver and said second metal in said second bed is silver.

8. The process according to claim 1, wherein said second metal in said first bed is tin and said second metal in said second bed is tin.

9. The process according to claim 1, wherein said first metal in said first bed is platinum and said first metal in said second bed is platinum.

* * * * *